United States Patent [19]
Hearn

[11] Patent Number: 6,110,741
[45] Date of Patent: Aug. 29, 2000

[54] GONADOTROPHIN RELEASOR HORMONE-CONTAINING COMPOSITION FOR EMBRYO CULTURE AND METHOD FOR IN VITRO FERTILIZATION

[75] Inventor: John P. Hearn, Madison, Wis.

[73] Assignee: Wisconsin Alumni Research Foundation, Madison, Wis.

[21] Appl. No.: 09/067,693

[22] Filed: Apr. 28, 1998

Related U.S. Application Data

[62] Division of application No. 08/654,723, May 29, 1996, Pat. No. 5,824,548.

[51] Int. Cl.⁷ .............................. C12N 5/00; C12N 5/02; C12N 5/06; C12N 5/08; C12N 5/10
[52] U.S. Cl. ..................... 435/363; 435/325; 435/366; 435/405; 435/431; 935/108
[58] Field of Search .................................. 435/325, 346, 435/363, 383, 387, 391, 404, 405, 366, 431; 935/108

[56] References Cited

U.S. PATENT DOCUMENTS

| | | | |
|---|---|---|---|
| 4,248,864 | 2/1981 | Jones | 424/177 |
| 5,096,822 | 3/1992 | Rosenkrans, Jr. et al. | 435/240.1 |
| 5,747,341 | 5/1998 | Brothers | 435/404 |

FOREIGN PATENT DOCUMENTS

| | | |
|---|---|---|
| 1570400 | 7/1980 | United Kingdom . |
| 2052258 | 1/1981 | United Kingdom . |

OTHER PUBLICATIONS

R. G. Edwards and S. A. Brody, "The Human Embryo in Vivo and in Vitro," Chap. 10 in *Principles and Practice of Assisted Human Reproduction*, W.B. Saunders Company, N. Y.: 1995, pp. 415–474 –published sufficiently before filing date such that the month is not an issue.

DeCherney, et al., "In Vitro Fertilization & Related Techniques," Chap. 56 in *Current Obstetric & Gynecologic Diagnosis & Treatment* ed. A. H. DeCherney and M. L. Pernoll, Appleton & Lange, Conn.: 1994, pp. 1026–1029 –published sufficiently before filing date such that the month is not an issue.

Seshagiri, et al., "The Secretion of Gonadotrophin–Releasing Hormone by Peri–Implantation Embryos of the Rhesus Monkey: Comparison with the Secretion of Chorionic Gonadotrophin," *Human Reproduction* vol. 9, No. 7, Jul./94, pp. 1300–1307.

Parker, et al., "Altered Cell Strains in Continuous Culture: A General Survey," *Special Publications of the New York Academy of Sciences* vol. V, 1957, pp. 303–313 –published sufficiently before filing date such that the month is not an issue.

P. B. Seshagiri and J. P. Hearn, "In–Vitro Development of In–Vivo Produced Rhesus Monkey Morulae and Blastocysts to Hatched, Attached, and Post–Attached Blastocyst Stages: Morphology and Early Secretion of Chorionic Gonadotrophin," *Human Reproduction* vol. 8, No. 2, Feb./93, pp. 279–287.

B. Lunenfeld, "Past Present and Future of Gonadotropins," in *Advances in Assisted Reproductive Technologies* ed. Mashiach et al., Plenum Press, N. Y.: 1990, pp. 39–45 –published sufficiently before filing date such that the month is not an issue.

Goodman and Gilman, "Adenophypophyseal Hormones and Related Substances," Chap. 56 in *The Pharmacological Basis of Therapeutics*, 8th Ed., 1993, pp. 1346–1353 –published sufficiently before filing date such that the month is not an issue.

M. M. Seibel, "A New Era in Reproductive Technology: In Vitro Fertilization, Gamete Intrafallopian Transfer, and Donated Gametes and Embryos," *The New England Journal of Medicine* vol. 318 No. 13, Mar./88, pp. 828–834.

J. P. Hearn, "The Embryo–Maternal Dialogue During Early Pregnancy in Primates," *J. Reprod. Fert.* vol. 76, 1986, pp. 809–819 –published sufficiently before filing date such that the month is not an issue.

Andreyko, et al., "Therapeutic Uses of Gonadotropin–Releasing Hormone Analogs," *Obstetrical and Gynecological Survey* vol. 42, No. 1, Jan. 1987, pp. 1–21.

Neveu, et al., "Ovarian Stimulation by a Combination of a Gonadotropin–Releasing Hormone Agonist and Gonadotropins for In Vitro Fertilization," *Fertility and Sterility* vol. 47 No. 4, Apr. 1978 pp. 639–643.

B. Lunenfeld and V. Insler, "Gonadotropin Releasing Hormone Pituitary Action: Agonists and Antagonists," in *Hormones in Gynecological Endocrinology* The Parthenon Publishing Group Inc., N. J.: 1992, pp. 17–27 –published sufficiently before filing date such that the month is not an issue.

Zhang, et al., "Effects of Intraventricular Injection of a LH–RH Analog on Pregnancy in Rats," Database Chemical Abstracts, File Server STN Karlsruhe, Abstract 99:64469, 1997 –published sufficiently before filing date such that the month is not an issue.

Bowers, et al., "Contraception and Inhibition of Ovulation by Minipump Infusion of the Luteinizing Hormone Releasing Hormone, Active Analogs and Antagonists," *Biochemical and Biophysical Research Communications* vol. 72, No. 3, 1976, pp. 1003–1007 –published sufficiently before filing date such that the month is not an issue.

(List continued on next page.)

*Primary Examiner*—David M. Naff
*Assistant Examiner*—Deborah K. Ware
*Attorney, Agent, or Firm*—Michael Best & Friedrich LLP; Teresa J. Welch

[57] ABSTRACT

In vitro incubation of primate embryos in the presence of added exogenous gonadotrophin releasor hormone (GnRH), results in enhanced chorionic gonadotrophin production associated with increased survival and attachment of the embryos. Treatment of in vitro fertilized embryos with GnRH can be used to improve implantation. Agonists of GnRH reduce attachment competence of embryos and are thereby useful as post-fertilization contraceptives.

7 Claims, 2 Drawing Sheets

OTHER PUBLICATIONS

Robert C. Jones, "Subcutaneous and Intrabursal Administration of an LRH Agonist to the Pregnant Hemicastrated Rat During Preimplantation," *International Journal of Fertility*, vol. 29, 1984, pp. 122–128 –published sufficiently before filing date such that the month is not an issue.

Begeot, et al., "Influence of Gonadoliberin on the Differentiation of Rat Gonodotrophs: An In Vivo and In Vitro Study," *Neuroendocrinology*, vol. 38, No. 3, 1984, pp. 217–225 –published sufficiently before filing date such that the month is not as issue.

Hung, et al., "Fibronectin in Reproduction," *Steroids*, vol. 54, No. 6, Dec. 1989, pp. 575–582.

GONADOTROPHIN RELEASOR HORMONE-CONTAINING COMPOSITION FOR EMBRYO CULTURE AND METHOD FOR IN VITRO FERTILIZATION

CROSS-REFERENCE TO RELATED APPLICATION

This application is a divisional of application Ser. No. 08/654,723, filed May 29, 1996 now U.S. Pat. No. 5,824,548.

This invention was made with United States government support awarded by the National Institute of Health (NIH), Grant No. RR00167. The United States Government has certain rights in this invention.

FIELD OF THE INVENTION

The present invention relates to the field of primate reproduction, and to an in vitro culture technique which enhances the rate of attachment of an embryo.

BACKGROUND OF THE INVENTION

In the field of infertility treatment, the development of in vitro fertilization techniques has enabled many couples to conceive and bear children whose infertility proved intractable to other treatments. In particular, in vitro techniques may be indicated in situations in which the fallopian tubes are irreversibly damaged, or where sperm is deficient in motility or concentration. More recently the indications for invitro fertilization have expanded, and may include endometriosis, immunological infertility, and cases of unexplained prolonged infertility. Since 1978 when the first child conceived from invitro ovum fertilization was born, there have been many advances in technique.

In general, the steps in in vitro fertilization involve induction of ovulation, retrieval of oocytes, the fertilization event, and transfer of the embryo to a receptive uterus. In inducing ovulation, hormonal regimens are adopted which increase the chances of hyperovulation, so that more than one oocyte reaching metaphase II is obtained. Two basic regimens involve administration of either human menopausal gonadotrophin (hMG) alone, or hMG in combination with clomiphene either simultaneously or sequentially. Serum estradiol is monitored to ensure progressive increase in serum levels with simultaneous monitoring by ultrasonography of the size of the follicles.

Lutinizing hormone (LH) levels are carefully monitored, and when follicular diameter reaches about 18 mm, human chorionic gonadotrophin is administered which induces a surge in LH associated with follicular maturation and ovulation. More recently, administration of gonadotrophin releasing hormone agonists (hGnRH-a) has been used to suppress pituitary activity during the two week period prior to administration of chorionic gonadotrophin (CG). This has improved pregnancy rates because there is dramatic reduction in premature LH surges associated with poor mature oocyte development. For a detailed description of the use of hGnRH agonists in controlling hyperovulation, see Lunenfeld, B, "Past Present and Future of Gonadotrophins," in *Advances in Assisted Reproductive Technologies*, ed. Mashiach et al., Plenum Press, N.Y.: 1990, at 39.

Recovery of oocytes is performed approximately 34 hours after administration of human chorionic gonadotrophin (hCG). Various ultrasound-guided techniques for oocyte aspiration have been developed and laparoscopy is rarely performed in current practice. Typically an ultrasound transducer is placed on the abdomen and a needle is passed through the abdomen and bladder, or alternatively, transvaginally, into the follicle. Maturity of each aspirated egg is estimated by assessing the compactness of the cumulus surrounding the oocyte. Those with a loosely expanded cumulus are deemed mature, and ready for fertilization after an initial 6 hour incubation in culture media. Those oocytes deemed immature are incubated an additional 24 to 30 hours.

Spermatozoa, washed in tissue culture medium to remove seminal fluid, are further incubated in a 5% carbon dioxide atmosphere for approximately 2 hours. During this period, the sperm cells become "capacitated" as demonstrated by hyperkinetic motility. Some 10–50,000 spermatozoa are then placed in the incubation chamber with the oocytes. Fertilized eggs appear with two pronuclei 15–17 hours post-insemination. Uterine or tubal deposition via cannula is usually carried out after further 37 to 72 hour incubation until the embryo attains the four to eight cell stage. For further details of the in vitro fertilization process, see Seibel, et al., *New England J. Med.,* 318: 828 (1988).

In spite of technical improvements at virtually every step of the invitro fertilization process, the success rate remains disappointingly low. After embryo transfer to the uterus, the implantation rate remains at only about 20–25 percent. There is some improvement in pregnancy rate when multiple embryos are transferred. However, this also increases the chance of multiple birth. It is widely thought that the low success rate results from subtle hormonal imbalances which make the embryo and/or uterus more or less receptive to implantation. Adjustment or better control of hormone responses has led to improvement in oocyte recovery and production in every step of the process except for implantation.

In the primate there are several hormonal systems involved in the reproductive cycle which may affect embryo implantation. Gonadotrophin releasing hormone, also referred to as gonadotrophin releasor hormone (GnRH) has a central function in regulating the reproductive process. GnRH synthesis occurs primarily in the arcuate nucleus region of the hypothalamus. It is transported to and released from the median eminence into the hypothalamic/hypophyseal portal system. Pulsatile production of GnRH stimulates release in the gonadotrope region of the anterior pituitary gland, of LH and follicle stimulating hormone (FSH) into the peripheral circulation.

In the ovary, the primordial follicle consists of an oocyte and an outer layer of granulosa cells. In response to FSH a recruited follicle forms gap junctions between the oocyte and the granulosa cell layer. Growth of the follicle progresses as the oocyte enlarges and the zona pellucida forms. Interestingly, the follicular fluid contains an aromatase enzyme system which can convert androgens to estrogen, which in turn increases the FSH receptor content of the follicle. The presence of estrogen and FSH in the follicle is essential for continued follicular growth. Since the dominant follicle has more FSH receptors, it competes favorably for free FSH which is continually declining in concentration due to estrogen suppression. Thus a dominant follicle emerges. The FSH also stimulates formation of LH receptors, and conversely, LH can stimulate production of its own receptors in FSH-primed cells.

A major function of the secreted estrogen is to maintain peripheral threshold concentrations of estradiol required for induction of the LH surge, prepatory to ovulation. LH stimulates reduction division in the oocyte and luteinization of the granulocyte layer. The LH surge is also associated with synthesis of progesterone and prostaglandins within the follicle which enhance the activity of enzymes involved in rupture of the follicular wall.

In the luteal phase, the formation and continued development of the corpus luteum is maintained by continued LH stimulation and by a surge in progesterone production. If pregnancy does not ensue, the corpus luteum rapidly degenerates at 9 to 11 days post-ovulation. If pregnancy ensues, production by the embryonic placenta of CG rescues the corpus luteum, maintaining the pregnancy. Detectable CG levels appear at the peak of corpus luteum development which stimulate steroid synthesis until placental steroidogenesis is well established by the 7th week of gestation.

Recently, Seshagiri, et al., *Human Repro.*, 9: 1300 (1994) discovered that the secretion of CG first by the embryonic trophoblast and subsequently by the placental syncytiotrophoblast cells is preceded by synthesis of GnRH. Immunocytochemical analysis showed that GnRH, detected as early as the pre-hatching blastocyst stage, was later localized exclusively in cytotrophoblasts and not in syncytiotrophoblasts, and may represent an early differentiation event in the primate peri-implantation embryo.

SUMMARY OF THE INVENTION

The present invention relates to a method for increasing the rate of implantation of primate embryos in a receptive uterus, and to certain media in which an embryo may be cultured in carrying out this method. A method is also disclosed for reducing the likelihood of embryo implantation, which may have contraceptive applications.

In particular, the present method of increasing survival of primate embryos in vitro comprises culturing a fertilized primate morula, blastomere, or blastocyst in the presence of gonadotrophin releasor hormone in a physiologically sufficient concentration from the time of its suspension in culture media to the implantation stage of the blastocyst. A physiologically sufficient concentration means that amount necessary to achieve attachment of greater than 90 percent of embryos on an empirical basis, but generally in the concentration range of 0.125 to 0.625 nM, based on the molecular weight of the capped decapeptide.

A further embodiment of the present invention provides for the foregoing embryo culture procedure together with the further steps of removing the blastocyst from culture prior to in vitro attachment and cell differentiation, and releasing it into a physiologically receptive uterus. Ordinarily the physiologically receptive uterus is that of the oocyte donor, which has been made receptive through the hormonal manipulations leading to ovulation. However, a hormonally primed surrogate may also be a recipient.

The present culture method is adaptable to in vitro fertilization of a primate oocyte and achievement of pregnancy in a receptive female according to conventional practice involving the steps of inducing hyperovulation by hormonal therapy, retrieving oocytes under laparoscopy or other standard or medically acceptable method, incubating the oocytes in vitro in a culture medium for a suitable period until the oocytes are cytologically mature for fertilization, fertilizing with freshly obtained or frozen, stored, newly capacitated sperm, incubating in enriched culture medium in the presence of gonadotropin releasor hormone in a concentration sufficient to stimulate chorionic gonadotrophin synthesis correlated with prolonged survival of viable primate embryos, incubation of the fertilized oocyte continuing from the time of double pronuclei visualization to the implantation stage of the mature blastocyst, harvesting the mature blastocyst from culture and releasing it into a physiologically receptive uterus.

The present invention also provides a culture medium, either in final aqueous form containing protein supplements, or as a defined base medium in dry form which can be reconstituted. The culture medium is an aqueous composition comprising a conventional culture medium supportive of embryo development supplemented with gonadotrophin releasor hormone. In a preferred embodiment, the aqueous composition for culturing primate embryos invitro comprises a culture medium containing inorganic salts in a physiologically compatible range of concentration, essential L-amino acids in nutritive concentrations, essential vitamins in concentrations supportive of embryonic growth, purine and pyrimidine sources in physiologic concentration, energy generating system cofactors, buffering agents, a metabolizable carbon source, a physiologically compatible protein carrier solution, and gonadotrophin releasor hormone in a concentration sufficient to stimulate chorionic gonadotrophin synthesis correlated with prolonged survival and enhanced attachment and implantation rates of viable primate embryos.

In dry form, the defined base culture medium comprises a powdered mixture containing inorganic salts, essential L-amino acids, essential vitamins, sources of purines and pyrimidines, energy generating systems cofactors, buffering agents, a metabolizable carbon source, all of which are present in such proportions that when reconstituted in aqueous 1×solution are in physiologically compatible concentrations, together with lyophilized gonadotrophin releasor hormone present in a proportion that when the powdered mixture is fully reconstituted, it is present in a concentration sufficient to stimulate chorionic gonadotrophin synthesis associated with prolonged survival and enhanced attachment and implantation rates of viable primate embryos.

The present method also provides a method for preventing uterine implantation of an embryo in a primates in which a gonadotrophin releasor hormone agonist is administered intravenously, intramuscularly, or transdermally in a dose sufficient to stimulate chorionic gonadotrophin production by the embryo. Stimulation of CG production is apparently not the only physiologic effect of the natural GnRH hormone, since treatment of embryos with an agonist results in reduction in uterine attachment competence of the embryo. A preferred agonist is [Dtry$^6$, Pro$^9$—NHEt]—GnRH.

DETAILED DESCRIPTION OF THE PREFERRED EMBODIMENT

Figure 1:
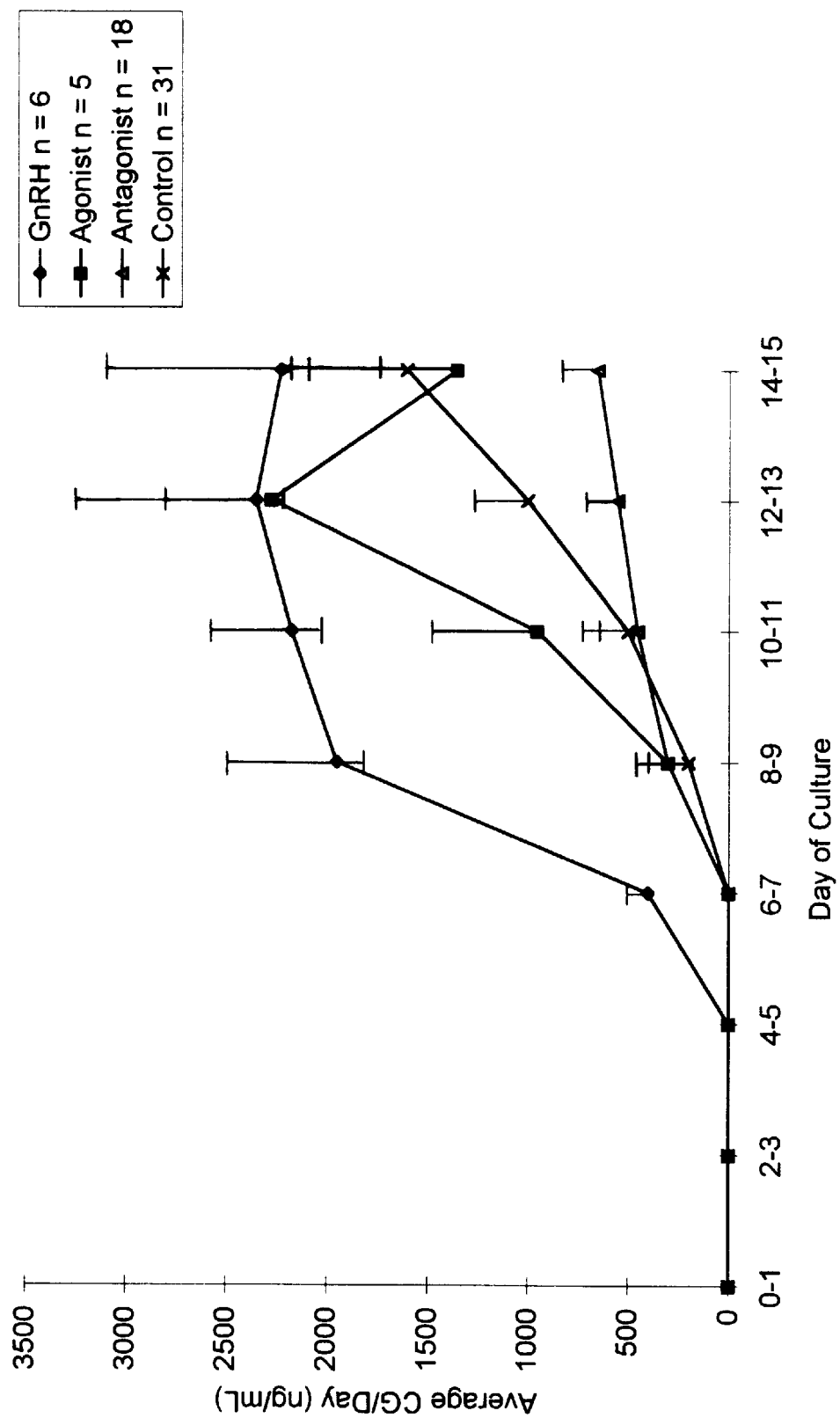
FIG. 1 is a rectilinear plot showing levels of CG measured in culture medium in which growing primate embryos are incubated in the presence or absence of GnRH, or a GnRH agonist or antagonist.

In vitro fertilization and transfer of the resultant embryo to a receptive uterus has become an increasingly acceptable way to overcome infertility from a variety of causes. The steps for carrying out the procedure generally include strategies for recovery mature oocytes, usually by aspiration from the ovary of multiple oocytes using a variety of techniques after hormonal therapies to cause hyperovulation, and then incubating the oocytes in vitro prior to introduction of sperm. Capacitated spermatozoa are then added and fertilization is allowed to occur. There is great variation in the techniques employed in these steps. For example, some clinics prefer to conduct all incubations in a 5% carbon dioxide environment, whereas others conduct the fertilization step at ambient atmosphere. Also, media will differ significantly in sodium bicarbonate concentration.

Similarly, different clinics use different criteria for evaluating the quality of embryos. Most clinics score embryos by stereomicroscopy only, whereas others chronicle possible disorders by use of high magnification microscopy, cytochemistry, and electron microscopy. A recent detailed review of the various scoring criteria, and the methods for recovery and incubation of embryos prior to and during fertilization is set forth in Edwards, et al., *Principles and Practice of Assisted Human Reproduction,* W. B. Saunders Company, N.Y.: 1995, hereby incorporated by reference. Also useful are Decherney, et al., *Current Obstetric & Gynecologic Diagnosis & Treatment,* Appleton & Lange, Connecticut: 1994, and Seibel, supra.

According to most authorities, after cleavage ensues, and timing of the initial divisions confirms the health of the embryo(s), they are then transferred at the four to eight cell stage to the uterus, generally through release from a cannula inserted through the cervix. In the studies described in the Example, primate (rhesus monkey) embryos are cultured in vitro until hatching and attachment occurs as shown by firm adhesion to the serum coated culture vessel, with formation of trophectodermal outgrowth. The culture times are considerably longer from initial deposit of the morulae or blastocytes in culture to observation of attachment, than the culture period in most in vitro fertilization procedures. This suggests that somewhat better implantation rates might be achieved by longer incubation times, until at least the blastocyst has expanded further to 275 to 425 $\mu$m in diameter. However, the possible increase in attachment competence of the embryo must be balanced against the fragility of the enlarged embryo structure after prolonged incubation. The better medical practice may be to transfer the embryo after only a few rounds of cleavage in the presence of GnRH.

Applicant has previously shown that secretion of CG occurs prior to blastocyst hatching and attachment, Seshagiri, et al., *Hum. Reprod.,* 8: 279 (1993) hereby incorporated by reference. Applicant has further shown that this secretion of CG is preceded by synthesis and secretion of detectable GnRH during the entire peri-attachment period, from morula to attached blastocyst stages. See Seshagiri, et al., *Hum. Reprod.,* 9: 1300 (1994) hereby incorporated by reference. Immunocytochemical staining showed that GnRH synthesis is localized in cytotrophoblast embryo-derived cells, and CG is secreted primarily by the syncytiotrophoblasts.

In accordance with the present invention, fertilized morulae and blastocysts are incubated invitro in the presence of exogenous GnRH provided in a concentration of 0.125 nM to 0.625 nM (150 to 750 pg/ml), preferably about 0.0375 nM, to achieve increased levels of progression to attachment and trophectodermal differentiation. By preincubation with exogenous GnRH, the control levels of in vitro attachment at prolonged culture periods up to 12 days of culture increased from 60–70% to greater than 90%. The actual concentration of GnRH required to achieve the functional attachment result, may vary from one primate species to another, but generally it will be in a physiologically sufficient amount to stimulate an enhanced secretion of CG detectable by at least day 6, and a dramatically increased secretion by days 8–9, which is correlated with prolonged survival of viable embryos. A physiologically sufficient amount of GnRH present exogenously in culture will produce at least 1000 ng/ml of CG, assayable in the culture medium by at least day 9 postculture.

In a preferred embodiment, GnRH is present in culture initially at a 0.125–0.375 nM concentration. If the assay at days 5–7 fails to produce the expected elevation in CG levels, an additional amount of GnRH may be added. Use of sequentially increasing amounts of GnRH or different amounts at different embryo stages is contemplated by this invention. Such variations in procedure may be efficacious for different species of primate. It is apparent that in vitro observation of as few as 6 embryos will suffice to define the physiologically sufficient dose. It is not anticipated that there is any upper bound on the concentration of GnRH which may be employed. Estimates of receptor numbers suggest that in the 0.125 nM to 0.625 nM range, there is ample hormone present to saturate the available receptors. In the in vitro situation, there is no evidence that levels of GnRH in excess of receptor saturation are in any way independently toxic, or inhibitory to growth of the embryo.

The medium for in vitro incubation of embryos is a composition containing inorganic salts, essential L-amino acids, vitamins, purine and pyrimidine sources, energy generating cofactors, a metabolizable carbon source, a protein carrier solution and gonadotrophin releasor hormone. The components of the medium are selected by their known nutritive properties and on empirical studies of cell culture. The object is to provide a medium which is supportive of every aspect of cell metabolism including every metabolite capable of transcellular membrane transport, even though the cell may have catabolic enzymes for synthesizing the metabolite. The objective is to mimic as closely as possible the nutritive environment of the uterus itself in which naturally occurring fluids contain a variety of nutritional, hormonal, and enzymatic components.

In some animal systems, media have been developed which are actually much simpler than complex defined media or media containing undefined protein mixtures such as fetal calf serum. For example, U.S. Pat. No. 5,096,822 discloses a medium in which most standard nutrients have been omitted, including even glucose which is found to be somewhat inhibitory to bovine embryos. In fact, it appears that several ingredients in complex media may be inhibitory such as certain amino acids. Accordingly, the terms "essential" as in essential amino acids or essential vitamins, or "physiologically compatible" as in physiologically compatible range of concentration means levels of the substances referred to which support some cellular biochemical process known in the art, and which do not disrupt or inhibit embryonic development. The metabolizable carbon source is generally glucose, but lactate and/or pyruvate may also be used. Thus, any base or supplemented medium which is found to support embryonic development in vitro will have efficacy in the present invention so long as it incorporates gonadotrophin releasor hormone as an ingredient.

One such medium from which good results are obtained in the primate system is CMRL 1066 media, manufactured by GibcoBRL, and first reported by Parker, et al., *Special Publications,* N.Y. Academy of Sciences, 5: 303 (1957) for the propagation of monkey kidney cells. The formula of the base media is given in Gibco Product Catalogue and Reference Guide, 1995–1996, at p. 1.61 hereby incorporated by reference and set forth in Table 1 below.

TABLE 1

| COMPONENTS | Conc. (mg/L) | Molarity (mM) |
|---|---|---|
| INORGANIC SALTS | | |
| Calcium chloride (CaCl$_2$) | 200.00 | 1.800 |
| Potassium chloride (KCl) | 400.00 | 5.300 |
| Magnesium sulfate (MgSO$_4$) | 97.70 | 0.814 |
| Sodium chloride (NaCl) | 6800.00 | 116.00 |
| Sodium bicarbonate (NaHCO$_3$) | 2200.00 | 26.20 |
| Sodium phosphate, mono. (NaH$_2$PO$_4$—H$_2$O) | 140.00 | 1.01 |
| OTHER COMPONENTS | | |
| Co-carboxylase | 1.00 | 0.0021 |
| Coenzyme A | 2.50 | 0.00326 |
| 2'Deoxyadenosine | 10.00 | 0.0398 |
| 2'Deoxycytidine | 10.00 | 0.0441 |
| 2'Deoxyguanosine | 10.00 | 0.0375 |
| Diphosphopyridine nucleotide (NAD) | 7.00 | 0.0105 |
| FAD (flavin adenine dinucleotide) | 1.00 | 0.00127 |
| D-Glucose | 1000.00 | 3.33 |
| Glutathione (reduced) | 10.00 | 0.0325 |
| 5-Methyl-deoxycytidine | 0.10 | 0.0004 |
| Phenol red | 20.00 | 0.0502 |
| Sodium acetate-3H$_2$O | 83.00 | 0.61 |
| Sodium glucuronate-H$_2$O | 4.20 | 0.0177 |
| Thymidine | 10.00 | 0.0413 |
| Triphosphopyridine Nucleotide (NADP) | 1.00 | 0.0013 |
| Tween 80 ® | 5.00 | — |
| Uridine 5'-triphosphate | 1.00 | 0.002 |
| AMINO ACIDS | | |
| L-Alanine | 25.00 | 0.281 |
| L-Arginine hydrochloride | 70.00 | 0.330 |
| L-Aspartic acid | 30.00 | 0.230 |
| L-Cysteine hydrochloride-H$_2$O | 260.00 | 1.48 |
| L-Cystine | 20.00 | 0.0833 |
| L-Glutamic acid | 75.00 | 0.51 |
| L-Glutamine | 100.00 | 0.685 |
| Glycine | 50.00 | 0.667 |
| L-Histidine hydrochloride-H$_2$O | 20.00 | 0.0952 |
| Hydroxy-L-proline | 10.00 | 0.0763 |
| L-Isoleucine | 20.00 | 0.153 |
| L-Leucine | 60.00 | 0.458 |
| L-Lysine hydrochloride | 70.00 | 0.383 |
| L-Methionine | 15.00 | 0.101 |
| L-Phenylalanine | 25.00 | 0.152 |
| L-Proline | 40.00 | 0.348 |
| L-Serine | 25.00 | 0.238 |
| L-Threonine | 30.00 | 0.252 |
| L-Tryptophan | 10.00 | 0.049 |
| L-Tyrosine 2Na 2H$_2$O | 58.00 | 0.260 |
| L-Valine | 25.00 | 0.214 |
| VITAMINS | | |
| Ascorbic acid | 50.00 | 0.284 |
| Biotin | 0.01 | 0.000041 |
| D-Calcium pantothenate | 0.01 | 0.000021 |
| Cholesterol | 0.20 | 0.000517 |
| Choline chloride | 0.50 | 0.0035 |
| Folic acid | 0.01 | 0.0000227 |
| i-Inositol | 0.05 | 0.0002 |
| Niacinamide | 0.025 | 0.00203 |
| Nicotinic acid (Niacin) | 0.025 | 0.0002 |
| Para-aminobenzoic acid | 0.05 | 0.0003 |
| Pyridoxal hydrochloride | 0.025 | 0.0001 |
| Pyridoxine hydrochloride | 0.025 | 0.00012 |
| Riboflavin | 0.01 | 0.0000266 |
| Thiamine hydrochloride | 0.01 | 0.0000297 |

1. Parker R. C., et al. (1957) Special Publications, N.Y. Academy of Sciences, 5, 303. (Note: values established by the Tissue Culture Association Standards Committee.)
Tween 80 ® is a registered trademark of I.C.I. Americas, Inc.

The medium is made 1×with water (and 20% v/v fetal calf serum). The medium may be supplemented with compatible protein carrier solutions such as, for example, fetal calf serum, maternal serum, or human albumin fraction V. A fully reconstituted medium is one, such as CMRL, in which a 1×solution is obtained taking into account the volume of all fluid ingredients, i.e. water, serum, or other protein solution.

Applicant has also discovered that culture of primate embryos in the presence of a GnRH agonist stimulates production of CG, but unexpectedly dramatically reduces the rate of embryo attachment and cell differentiation. The effect is severe enough to suggest that GnRH agonists may have utility as a contraceptive when administered by injection, or by transdermal appliances. An effective dose of GnRH agonists in suppressing premature LH surges during hyperovulation protocols is about 1 mg/day. A similar or somewhat higher dose up to about 7.5 mg may be necessary to achieve in vivo, the CG response associated with reduced rates of embryo attachment. For detailed information on dosage parameters for administration of gonadotrophins, and commercial sources of pharmaceutical grade hormones, see Goodman and Gilman, *The Pharacological Basis of Therapeutics*, 8th Ed., 1993, at Chapt. 56 hereby incorporated by reference. In the United States only one such agonist preparation is currently being marketed. Leuprolide acetate is available as an aqueous solution for subcutaneous infection. The preferred agonist in the present invention is [Dtrp$^6$, Pro$^9$ —NHEt]—GnRH, a form of leuprolide. Other agonists which may be used include Buserelin, Nafarelin, Lutrelin, Histrelin, or Triptorelin. Other advantages of the present invention will be apparent from the Example which follows.

EXAMPLE

Rhesus monkeys (*Macaca Mulatta*) were housed in pairs with controlled light (11L: 13D), temperature (22–25° C.) and humidity. Females were paired with fertile rhesus males from day 9 of the menstrual cycle until the breakdown of sex-skin colour. The day following the LH surge determined by radioimmunoassay was designated as day 0 of pregnancy as described in Seshagiri et al., *Am. J. Primatol.*, 29: 81 (1993).

Uterine-stage embryos were recovered by non-surgical uterine flushing carried out in the morning on day 5 (morulae) or 6 (blastocysts) of pregnancy according to the method described in Goodeaux, *J. Med. Prinitol.*, 19: 59 (1993). Females were lightly anaesthetized with ketamine (10 mg/kg body weight) and trans-cervical cannulation was achieved using a dilator (2×150 mm). The perforated end of a cell sampler (Curity No. 4860) was placed into the uterine lumen and the dilator was removed. A polyethylene tube (PE50) was threaded through the cell sampler and the uterine lumen was flushed with 30 ml of Dulbecco's phosphate buffered saline (Gibco, Grand Island, N.Y., USA). The flushings were collected into an evaporating dish and processed to recover embryos.

Zona-intact normal morulae or early blastocysts were cultured individually in tissue culture dishes (Falcon, Lincoln Park, N.J., USA) for ≧14 days in a humidified atmosphere of 5% CO$_2$ in air at 37° C. containing either 0.5 or 1 ml of CMRL-1066 medium supplemented with 20% bovine fetal serum (Gibco). Medium was changed on alternate days. While changing with fresh medium, aliquots (0.2 ml) of spent media (referred to below as media) were stored for GnRH estimation at −80° C. in assay tubes containing 0.3 mM bacitracin to prevent proteolytic degradation. All morphological evaluations of embryo development were carried out either daily or on alternate days using a Nikon Diaphot microscope equipped with Nomarski and phase contrast optics.

GnRH in spent media samples cultured with embryos was measured by a well-standardized, sensitive radioimmunoassay using antiserum R1245 (a gift from Dr. T. Nett, Colorado State University, Fort Collins, Colo., USA) as described in *Endocrinology*, 123: 1808 (1988). Synthetic GnRH (Rechelieu Laboratory, Inc., Montreal, Canada) was used for preparing both the [$^{125}$] GnRH and the reference standard. The standard curve was constructed using the embryo culture medium as a part of the radioimmunoassay buffer. The sensitivity was 0.1 pg/tube. The intra- and inter-assay coefficients of variation were 6.0 and 9.5%, respectively.

Biologically active CG was measured by the mouse Leydig cell in vitro bioassay as described in Seshagiri and Hearn, *Hum. Reprod.*, 8: 279 (1993). A 100 μl suspension of mouse Leydig cells (=40,000 viable cells) in medium 199/0.2% bovine serum albumin (BSA) medium was added to radioimmunoassay tubes containing either standard concentrations of human CG (CR-125: 14 900 IU/mg) or suitably diluted aliquots of the embryo grown/spent media samples or blank embryo culture medium. The tubes were incubated in a water-bath for 2 h at 33–36° C. and then the standard, control and test samples were analyzed for testosterone by a standard radioimmunoassay. The bioassay was validated using internal human CG standards and serial dilutions of sera from pregnant/ovariectomized monkeys. The sensitivity was 10 pg human CG/tube. The inter-assay variation was 9.1%.

In the present experiments in which the secretion of CG was monitored, a total of 60 rhesus embryos were obtained as indicated above, and divided into four incubation groups. A group of 6 embryos were cultured in media containing 0.375 nM gonadotrophin releasor hormone, 5 were cultured in media containing an equivalent amount of the agonist [Dtrp$^6$, Pro$^9$—NHEt]—GnRH, 18 were cultured in media containing 3.5 mM of the antagonist [Nal—Glu], and 31 were cultured in plain CMRL 1066 media. Incubations were carried out for 15 days. The results are graphed in FIG. 1, and show that embryos incubated in the presence of GnRH exhibit a profound increase in CG beginning as early as days 4–5. Synthesis continues to increase sharply through day 9, with a levelling off at about days 10–11. In contrast, the untreated controls show a much slower increase in the rate and magnitude of CG secretion beginning at about days 6–7, and rising to only about ⅔ the level attained by the GnRH treated group. The agonist appears to stimulate both the rate and magnitude of CG synthesis, but the antagonist shows a marked suppression of CG secretion.

Figure 2:
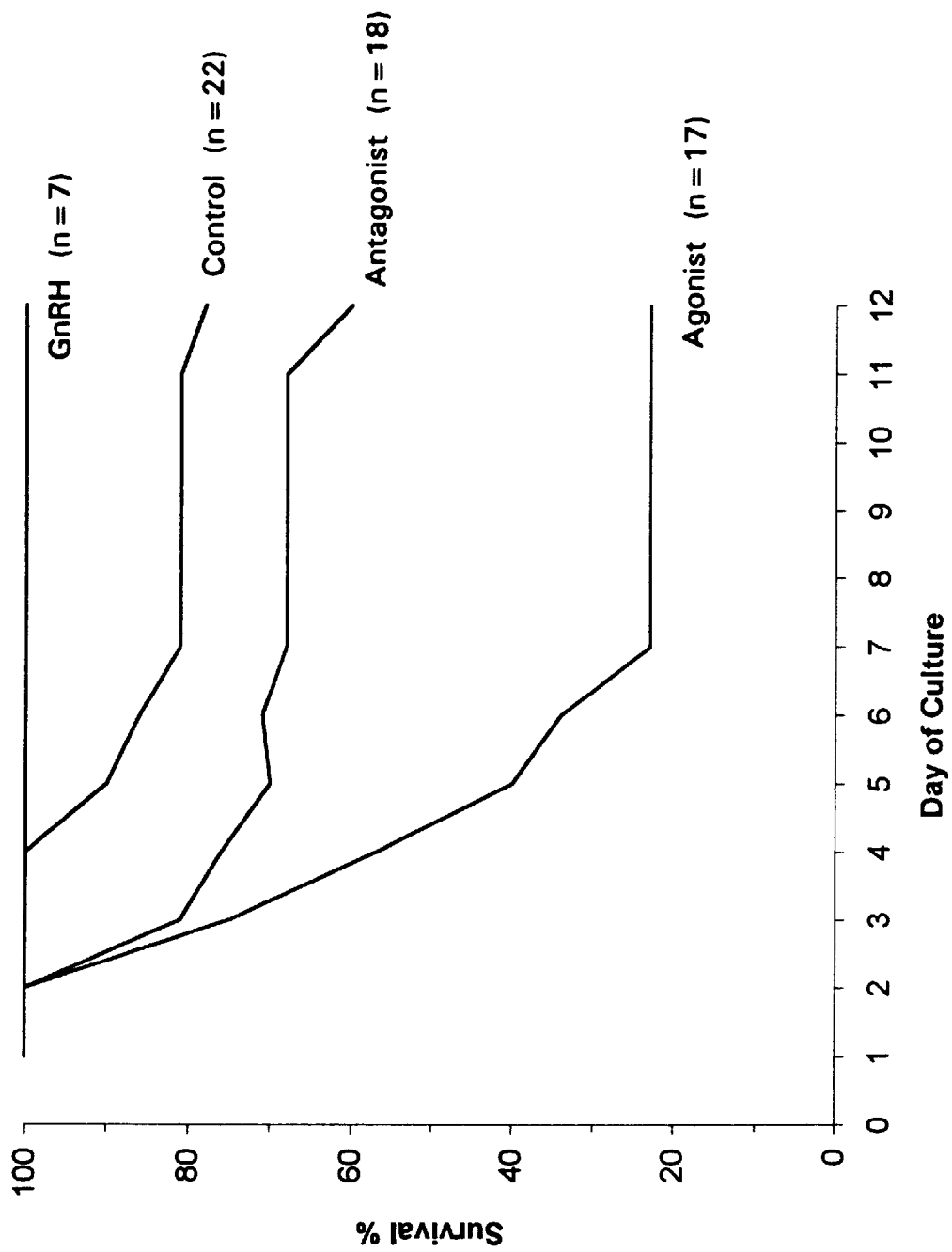
FIG. 2 is a rectilinear plot showing the percent survival of embryos cultured in the presence or absence of GnRH or a GnRH agonist or antagonist over a time course of 2 to 12 days incubation.

FIG. 2 depicts the survival data for a group of GnRH treated embryos (n=7), a control group of untreated embryos (n=22), and groups of antagonist and agonist treated embryos (n=18 and n=17 respectively). Virtually 100% of the GnRH treated embryos survived to 12 days, and demonstrated normal attachment and cell differentiation, compared to only about 80% of control embryos. In fact, the effect of GnRH on increased survival is deemed efficacious if greater than 90% of embryos survive.

FIG. 2 also illustrates the effect of agonist and antagonist treatment. Incubation with the agonist actually reduced survival even below the level of the antagonist, suggesting that GnRH itself has a direct or indirect effect on embryo survival at least to some extent independent of the role of GnRH in stimulating CG secretion. In the use of GnRH agonists in a typical hyperovulation regimen, the a 1 mg dose is administered weekly up to the point of oocyte harvest. Clearly use of the agonist as a contraceptive must occur after ovulation and before normal implantation of the embryo takes place. Therefore, this method of contraception may have particular efficacy after instances of unprotected intercourse.

What is claimed is:

1. An aqueous composition for culturing primate embryos in vitro comprising a culture medium capable of supporting embryo development supplemented with added exogenous gonadotrophin releasor homone in an effective concentration to increase the survival of viable primate embryos cultured in the gonadotrophin releasor hormone-supplemented culture medium, relative to the survival of embyros cultured in an unsupplemented culture medium.

2. The composition of claim 1 wherein said culture medium contains inorganic salts in a physiologically compatible range of concentration, essential L-amino acids in nutritive concentrations, essential vitamins in concentrations supportive of embryonic growth, purines and pyrimidine in physiologic concentration, coenzymes, buffering agents, a metabolizable carbon source; and supplemented with a physiologically compatible protein carrier solution.

3. The composition of claim 2 wherein said protein carrier solution is selected from the group consisting of fetal calf serum, horse serum, human serum albumin, and bovine serum albumin.

4. The composition of claim 1 or 2, wherein said gonadotrophin releasor hormone is present in a concentration of 150 to 750 pg/ml.

5. A defined base culture medium for use in culturing primate embryos in vitro comprising a powered mixture containing i) inorganic salts, essential L-amino acids, essential vitamins, purines and pyrimidines, coenzymes, buffering agents, a metabolizable carbon source, in proportions such that in fully reconstituted aqueous solution, said inorganic salts, said essential L-amino acids, said purines and pyrimidines, said coenzymes, said buffering agents, said metabolizable carbon source are contained in such solution in physiologically compatible concentrations; and ii) lyophilized gonadotrophin releasor hormone in a proportion that when said powered mixture is fully reconstituted said gonadotrophin releasor hormone is present in a concentration sufficient to stimulate chorionic gonadotrophin synthesis associates with prolonged survival of viable primate embryos.

6. In a method of carrying out in vitro fertilization of a primate oocyte and achievement of pregnancy in a receptive female according to the following steps: inducing hyperovulation by hormonal therapy, retrieving incubating the oocytes in vitro in a culture media, fertilizing the oocytes with freshly obtained, capacitated sperm to obtain primate embryos incubating the primate embryos from the time of double pronuclei visualization to the implantation stage of the mature blastocyst, harvesting the blastocyst from the culture media and releasing it into a physiologically receptive uterus, the improvement comprising carrying out said incubating of said primate embryos in the presence of exogenous gonadotrophin releasor hormone added to the culture media in an effective concentration to increase survival of viable primate embryos.

7. The method of claim 6 wherein said gonadotrophin releasor hormone is present at a concentration of 150 to 750 pg/ml.

* * * * *

UNITED STATES PATENT AND TRADEMARK OFFICE
CERTIFICATE OF CORRECTION

PATENT NO : 6,110,741
DATED : August 29, 2000
INVENTOR(S): John P. Hearn

It is certified that error appears in the above-identified patent and that said Letters Patent are hereby corrected as shown below:

In claim 6, line 50, after "retrieving", insert -- oocytes,--
on, line 53, after "embryos" insert -- , --

Signed and Sealed this

First Day of May, 2001

Attest:

NICHOLAS P. GODICI

Attesting Officer

Acting Director of the United States Patent and Trademark Office